(12) United States Patent
Kirby (10) Patent No.: US 8,041,429 B2
(45) Date of Patent: Oct. 18, 2011

(54) SYSTEM AND METHOD FOR CONTROLLING HYPOTHALAMIC FUNCTION VIA VESTIBULAR STIMULATION

(75) Inventor: Todd Kirby, Spring Church, PA (US)

(73) Assignee: RIC Investments, LLC, Wilmington, DE (US)

( * ) Notice: Subject to any disclaimer, the term of this patent is extended or adjusted under 35 U.S.C. 154(b) by 518 days.

(21) Appl. No.: 11/581,670

(22) Filed: Oct. 16, 2006

(65) Prior Publication Data

US 2007/0167985 A1    Jul. 19, 2007

Related U.S. Application Data

(60) Provisional application No. 60/727,809, filed on Oct. 18, 2005.

(51) Int. Cl.
*A61N 1/18* (2006.01)

(52) U.S. Cl. .............................. 607/45; 607/2
(58) Field of Classification Search ........................ 607/2
See application file for complete search history.

(56) References Cited

U.S. PATENT DOCUMENTS

| | | | | |
|---|---|---|---|---|
| 6,314,324 | B1 * | 11/2001 | Lattner et al. | 607/42 |
| 6,586,478 | B2 | 7/2003 | Ackman et al. | |
| 6,708,064 | B2 * | 3/2004 | Rezai | 607/45 |
| 6,748,275 | B2 * | 6/2004 | Lattner et al. | 607/42 |
| 6,878,111 | B2 * | 4/2005 | Kenknight et al. | 600/300 |
| 6,946,452 | B2 * | 9/2005 | Xu et al. | 514/62 |
| 7,300,449 | B2 * | 11/2007 | Mische | 606/198 |
| 7,580,752 | B2 * | 8/2009 | Gerber et al. | 607/41 |
| 2002/0156501 | A1 * | 10/2002 | Grey et al. | 607/2 |
| 2005/0075669 | A1 * | 4/2005 | King | 607/2 |

OTHER PUBLICATIONS

U.S. Appl. No. 60/642,367, filed Jan. 7, 2005, Paul et al.
U.S. Appl. No. 11/327,062, filed Jan. 6, 2006, Paul et al.
Fuller et al., "Neurovestibular modulation of circadian and homeostatic regulation: Vestibulohypothalamic connection?", PNAS, Nov. 26, 2002, pp. 15723-15728, vol. 99, No. 24.
Horowitz et al., "Nedial vestibular connections with the hypocretiin (orexin) system.", J Comp Neurol., Jun. 27, 2005, pp. 127-146.
Riccio et al., "Functional Transcutaneous Electrical Stimulation of the Vestibular System (U)", Armstrong Laboratory, Aug. 1995.
Dzendolet, "Sinusoidal Electrical Stimulation of the Human Vestibular Apparatus", Perceptual and Motor Skills, 1963, pp. 171-185, vol. 17, Southern Universities Press.
Mignot et al., "Sleeping with the hypothalamus: emerging therapeutic targets for sleep disorders", Nov. 2002, pp. 1071-1075, vol. 5, Stanford University Center for Narcolepsy.
Gerashchenko et al., "Role of the lateral hypothalamus in sleep", Sleep and Biological Rhythms, 2004, pp. S25-S26, Japanese Society of Sleep Research.
Peyron et al., "Neurons Containing Hypocretin (Orexin) Project to Multiple Neuronal Systems", The Journal of Neuroscience, pp. 9996-10015, Dec. 1, 1998, Society for Neuroscience.
PCT Search Report and Written Opinion, Oct. 1, 2007.

* cited by examiner

*Primary Examiner* — Carl H Layno
*Assistant Examiner* — Jeremiah Kimball
(74) *Attorney, Agent, or Firm* — Timothy Nathan (57) ABSTRACT

A system and method for regulating one or more physiological functions controlled by a hypothalamus of an individual. In one embodiment, a stimulation is applied to at least a portion of a vestibular system of the individual, a subjective input is received from the individual based upon the individual's perceived response of the hypothalamus in regulating the one or more physiological functions, and the stimulation is adjusted based on the received subjective input.

4 Claims, 6 Drawing Sheets

SYSTEM AND METHOD FOR CONTROLLING HYPOTHALAMIC FUNCTION VIA VESTIBULAR STIMULATION

CROSS-REFERENCE TO RELATED APPLICATIONS

This application claims priority under 35 U.S.C. §119(e) from provisional U.S. patent application No. 60/727,809 filed Oct. 18, 2005, the contents of which are incorporated herein by reference.

BACKGROUND OF THE INVENTION

1. Field of the Invention

The present invention relates to the treatment of a patient to regulate one or more physiological and/or psychological functions controlled by the hypothalamus by means of vestibular stimulation.

2. Description of the Related Art

Known systems and methods of vestibular stimulation are disclosed in U.S. Pat. Nos. 6,748,275 and 6,314,324 to Lattner et al. These patents disclose an apparatus and method in which the portions of the labyrinth associated with the labyrinthine sense and/or the nerves associated therewith are stimulated to augment or control a patient's respiratory function, open the patient's airway, induce or promote sleep, counteract vertigo, or a combination of these functions. For example, the treatment of insomnia is achieved by stimulating the vestibular system such that the patient perceives a rocking sensation. The present inventor recognized that there are further applications for use of vestibular stimulation above and beyond that taught by these patents.

SUMMARY OF THE INVENTION

One aspect of the invention relates to a system or method for regulating one or more physiological functions controlled by a hypothalamus of an individual. In one embodiment, the system comprises a vestibular stimulation element, a response module, and a control unit. The vestibular stimulation element applies a stimulation to at least a portion of the vestibular system of the individual. The response module enables an individual to provide a subjective input based upon a perceived response of the hypothalamus in regulating the one or more physiological functions, the response of the hypothalamus being in response to the stimulation applied to the vestibular system. The control unit controls the vestibular stimulation element such that the stimulation applied by the vestibular stimulation element is adjusted based on the subjective input provided to the response module. The method of this embodiment comprises regulating one or more physiological functions controlled by the hypothalamus using such a system, which includes applying a stimulation to at least a portion of a vestibular system of the individual, receiving a subjective input from the individual based upon the individual's perceived response of the hypothalamus in regulating the one or more physiological functions, and adjusting the stimulation based on the received subjective input.

Another aspect of the invention relates to a system and method for regulating one or more physiological functions controlled by a hypothalamus of an individual. In one embodiment, the system comprises a vestibular stimulation element, a response module, and a control unit. The vestibular stimulation element applies a stimulation to at least a portion of a vestibular system of the individual. The response module comprises a sensor that detects changes in a physiological function that is regulated by the hypothalamus in response to the stimulation applied to the vestibular system. The physiological functions comprise at least one of a vascular tone, a core temperature, a metabolic function, a pulse rate, a galvanic skin response, a heart rate variability, a baroreceptor sensitivity, a body weight, a muscle sympathetic nerve activation, a pupillary dilation, peristaltic movement of materials through the patient's digestive system, or a blood pressure. The control unit controls the vestibular stimulation element such that the stimulation applied by the vestibular stimulation element is adjusted based on detected changes in the physiological function. The method of this embodiment includes regulating one or more physiological functions controlled by a hypothalamus of an individual using such a system, which includes applying a stimulation to a vestibular system of the individual, detecting changes in a physiological function that is regulated by the hypothalamus in response to the stimulation applied to the vestibular system, and adjusting the stimulation based on the detected changes in the physiological function.

Another aspect of the invention relates to a system for influencing a hypothalamus of an individual to alleviate an anxiety level of the individual. In one embodiment, the system comprises a vestibular stimulation element, a response module, and a control unit. The vestibular stimulation element applies a stimulation to at least a portion of the vestibular system of the individual. The response module enables the individual to provide a subjective input based upon a perceived response of the hypothalamus in affecting the anxiety level of the individual, the response of the hypothalamus being in response to the stimulation applied to the vestibular system. The control unit controls the vestibular stimulation element such that the stimulation applied by the vestibular stimulation element is adjusted based on the subjective input provided to the response module.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
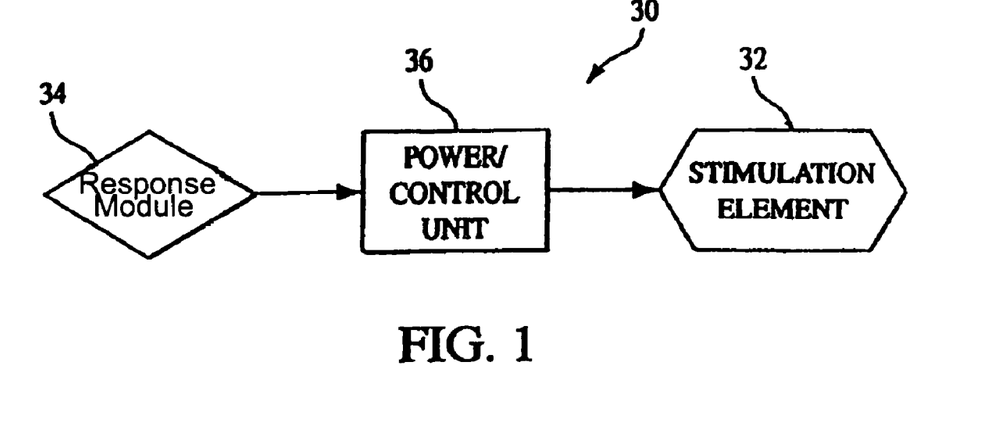
FIG. 1 is a schematic diagram of a vestibular stimulation system according to one embodiment of the present invention.

FIG. 1 schematically illustrates an exemplary embodiment of a vestibular stimulation system 30 according to the principles of the present invention. Vestibular stimulation system 30 is a device that stimulates portions of the labyrinth associated with the labyrinthine sense and/or associated nerves to provide a therapeutic benefit to the patient. More specifically, the present invention contemplates stimulating, either invasively or non-invasively, the receptors of the labyrinth associated with the labyrinthine sense and/or the nerves or nerve branches associated with such receptors, including the saccule, utricle, semicircular canals, vestibular nuclei, vestibular nerve and its nerve branches.

The present invention contemplates providing stimulation to at least one of these stimulation sites to elicit a desired response from the hypothalamus of the patient. The desired response may include one or more physiological and/or psychological effects, as will be described below. However, a general description of the stimulation system of the present invention is first provided. It should be noted that the stimulation system of the present invention is referred to through the present disclosure as a "vestibular stimulation system" because the stimulation sites of interest in the present invention are the above-identified structures and/or tissues of the human inner ear associated with the labyrinthine sense, which is commonly referred to as the vestibular system.

As shown in FIG. 1, vestibular stimulation system 30 includes the following three components: a stimulation element 32 that performs the actual stimulation of the tissue, a response module 34 to monitor a response of the patient's hypothalamus, and a power/control unit 36 that receives the signals provided by response module 34 and causes stimulation energy to be provided to stimulation element 32 at an appropriate timing, level, pattern, and/or frequency to achieve the desired physiological function.

Stimulation element 32 is any device or combination of devices that provides a controlled stimulation to a target site. As noted above, the particular stimulation sites of interest in the present invention are one or more of the following and/or a combination thereof: the vestibular nerve, portions of the vestibular nerve, the branches of vestibular nerve or portions thereof, each of the semicircular canals (anterior, posterior, and lateral) or portions thereof, the common limb, utricle, saccule, and ampullae. It is to be understood that the precise stimulation site or sites, as well at the method in which the sites are stimulated, will vary depending on the desired response of the hypothalamus to be achieved.

Stimulation of each of these tissues can be provided on the surface, internally, or in nearby tissues or structures. In addition, depending on the stimulation technique used, the stimulation devices can be completely invasive, completely non-invasive, or a combination thereof.

The present invention contemplates stimulating one or more of the above stimulation sites using one or more of a variety of stimulation techniques, such as electrical, mechanical, magnetic, thermal, chemical, radio frequency, or infrared stimulation. The specific mechanism or combination of mechanisms for delivering the stimulation will depend on the stimulation technique used, which will depend on the stimulation site selected. The following are examples of suitable stimulation techniques and their stimulation mechanism that can be used in the vestibular stimulation system of the present invention to stimulate one or more of the stimulation sites identified above:

Electrical Stimulation—The present invention contemplates providing electrically conductive electrodes in, on, and/or near the tissue to be stimulated so that an electric current can be delivered to the adjacent tissue via the electrode. The electrodes can be invasive, non-invasive, or a combination there. The electrodes can be placed near the vestibular system and/or at other locations on the patient, such as the forehead, so long as a stimulation energy is delivered to the patient's vestibular system. The electrode or electrodes can have a variety of sizes and configurations depending on the stimulation pattern to be provided. For example, a point electrode can be used to stimulate a very specific site, or a spot or strip electrode can be provided to induce stimulation over a larger area. U.S. Provisional Patent Appln. No. 60/642,367 filed Jan. 7, 2005 and U.S. patent application Ser. No. 11/327, 062 filed Jan. 6, 2006 disclose an "ear bud" type of stimulation electrode suitable for use in the present invention, in which the electrode is situated in the ear canal.

The present invention further contemplates providing electrical stimulating using a current controlled source, in which the current output to the electrode is monitored. The current source automatically adjusts the current to keep it at or near the desired current level if, for example, the resistance of the patient changes.

In addition, the present invention contemplates using a microstimulator electrode that is inserted at the stimulation site and that receives power and control data from an external source, such as an rf field created by an external oscillator.

A specific type of a strip electrode that can be used in the present invention to stimulate a nerve is an electrode cuff that completely or partially surrounds a nerve or nerve branch to be stimulated. Because the cuff surrounds to target nerve, it allows the stimulation energy to be delivered through the nerve tissue while minimizing collateral stimulation of other tissues. Of course, multiple electrodes and electrode pairs can be provided to achieve the desired stimulation pattern over the desired area to be stimulated. In addition, the present invention contemplates inserting one or more needle electrodes into the inner ear for selective simulation of a nerve, nerve branch, or a global area, such as the saccule, to promote the desired hypothalamic response. A needle electrode has the advantage of being able to target a specific location for stimulation.

Mechanical Stimulation—The present invention contemplates placing a pressure application device, such as an inflatable balloon, near the tissue to be stimulated so that inflating the balloon applies a pressure on the adjacent tissue. This type of mechanical stimulation system provides pressure fluctuations to the patient to promote a particular sensation. Another example of a pressure application device particularly well suited for use with the semicircular canal or with a nerve is a pressure cuff, which is placed either completely or partially around the canal or nerve to be stimulated so that inflating the pressure cuff exerts pressure on the underlying portion of the semicircular canal or nerve. Yet another mechanical stimulation device is a vibrating element that produces a mechanical vibration at a selected frequency.

Sonic Stimulation—The present invention also contemplates stimulating the vestibular area or specific sites within this area using a sonic or ultrasonic device that delivers stimulation on a carrier wave typically above 20,000 Hz, which is not in the audible range for humans.

Magnetic Stimulation—The present invention further contemplates providing a magnetic field generator in the form of one or more coils in and/or near the inner ear. The coils generate a time varying magnetic field that creates a spatially varying electric field that induces stimulation in the target tissue. In addition, focusing elements, such as ferromagnetic material implants, can be provided in or near the targeted tissue to focus or shape the magnetic field, and, hence the electric field, at a specific location.

Thermal Stimulation—The present invention contemplates providing a stimulation device that uses changes in temperature to induce stimulation of the patient's tissue. Examples of devices that induce a temperature change include a laser, infrared device, or a device that dispenses heated or chilled liquid to the stimulation site.

Chemical Stimulation—The present invention further contemplates providing a device that introduces chemicals or that causes chemical reactions at a stimulation site to control the stimulation at that site. For example, an injection or medicine pump can be provided at the inner ear to introduce the desired stimulation medication at the stimulation site.

Radio-Frequency Stimulation—The present invention still further contemplates using radio frequency wavelengths generated by a suitable device to provide the desired stimulation. For example, as noted above, stimulation can be induced by providing power and control data using radio frequencies (rf) received by one or more microstimulators implanted in the patient. Different microstimulators implanted at different locations in the patient can be tuned to different frequencies so that a wide variety of stimulation patterns can be achieved.

Infrared Stimulation—The present invention also contemplates using infrared technology to deliver the stimulation to the patient's tissues. Short wave, 7,200-15,000 .ANG., or long wave, 15,000-150,000 .ANG., systems can be used to deliver the stimulation to the target site.

It is to be understood that this list of stimulation techniques is not exhaustive or exclusive. On the contrary, the present invention contemplates using any stimulation technique or device that, when actuated, provides the desired stimulation function. The selection and different types of suitable stimulation devices suitable for use in achieving the desired physiological function of the present invention will be better understood from the discussion of the particular implementations of the stimulation system of the present invention provided below.

Response module 34 may include one or more devices that detect one or more physiological functions of the patient and provides this information to power/control unit 36. It can be appreciated that the specific type of devices used in response module 34 with the stimulation system of the present invention to monitor one or more of these functions will depend on one or more physiological functions of interest. Nevertheless, examples of suitable devices for use with the present invention include devices capable of monitoring a vascular tone, a core temperature, a metabolic function, a pulse rate, a galvanic skin response, a heart rate variability, a baroreceptor sensitivity, a body weight, a muscle sympathetic nerve activation, a pupillary dilation, peristaltic movement of materials through the patient's digestive system, or a blood pressure of the patient.

It is to be understood that this list of suitable sensors is also not exhaustive or exclusive. On the contrary, the present invention contemplates using any device that is capable of detecting or monitoring a physiological function of the patient of interest, such as the a physiological function controlled by an autonomic nervous system of the patient, and that provides a signal indicative thereof. As with stimulation element 32, the selection and different types of suitable devices for use in response module 34 with each embodiment of the present invention can be appreciated from the discussions of the particular implementations of the stimulation system of the present invention.

Power/control unit 36 is any device that provides stimulation energy to the patient via the stimulation element and that is capable of controlling the application of this energy. For example, power/control unit 36, is, in one embodiment of the present invention, a rechargeable battery with a pulse shaping device that modulates the shape, frequency and amplitude of pulses of stimulation energy provided to the stimulation element by the battery. The power/control device preferably also includes a processor that is capable of receiving signals from response module 34 and controlling the application of stimulation energy, i.e., the shape, time, frequency, and/or amplitude of the pulses applied to the stimulation element, based on the signals from response module 34 to achieve the desired response from the hypothalamus.

The present invention contemplates that power/control unit 36 can include an "intelligence" capability that provides relatively complex control functions, such as adaptively controlling the stimulation energy, compensating for changes in monitored parameters, allowing the user to specify the control ranges, and detecting between events of interest, such as changes, a lack of changes, in the one or more physiological functions and/or psychological functions being monitored by response module 34. For example, in an exemplary embodiment of the present invention, the user or manufacturer provides the power/control unit with the stimulation parameters, such as intensity, frequency, interpulse duration, for the stimulation energy to be provided to the patient. Thereafter, these parameters are changeable by the patient or adaptively changeable by the control unit so that the target nerve firing rate is controllable to create the desired stimulation function.

A variety of control techniques can be used to provide this intelligent capability, such as fixed parameter control, where the control unit causes a certain action if a particular parameter is detected, threshold based control where the control unit compares an input signal to a threshold to determine if an action is required, rule based control, fuzzy logic, and neural network control. Power/control unit 36 can be provided outside the patient, entirely within the patient, or a combination thereof. Details of the function of the power/control unit to control the stimulation energy provided to the patient and specific examples of this device are discussed below.

Figure 2:
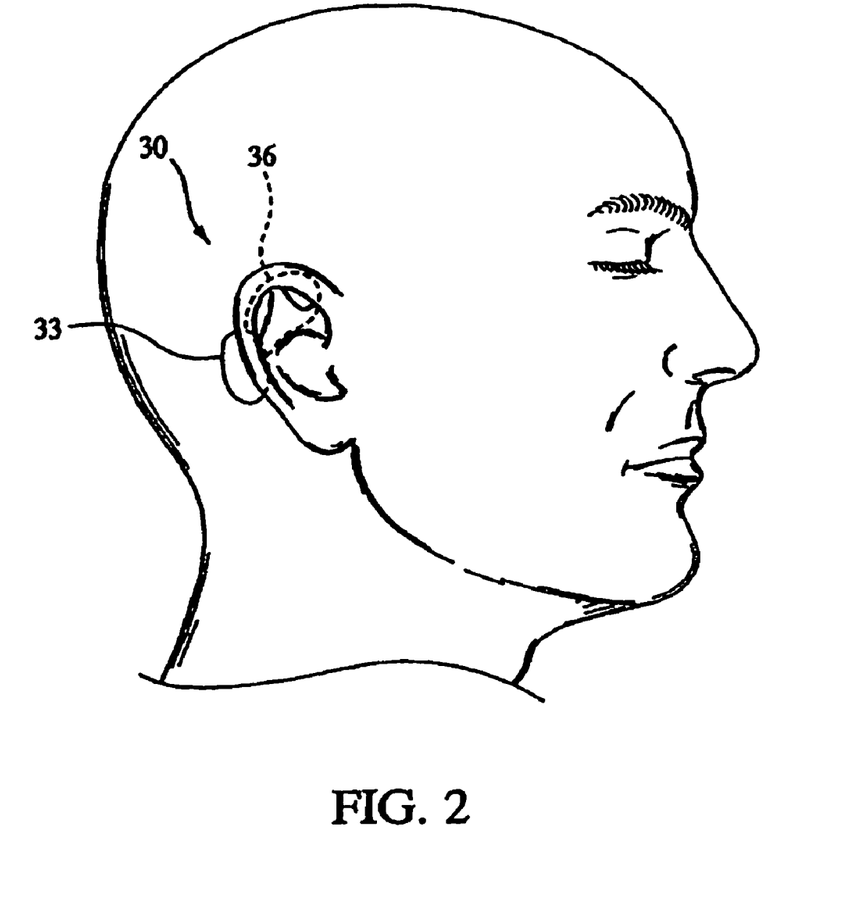
FIG. 2 is a side view of a human head showing the positioning of a non-invasive vestibular stimulation system using surface electrodes as a stimulating element according to one embodiment of the present invention.
Figure 3:
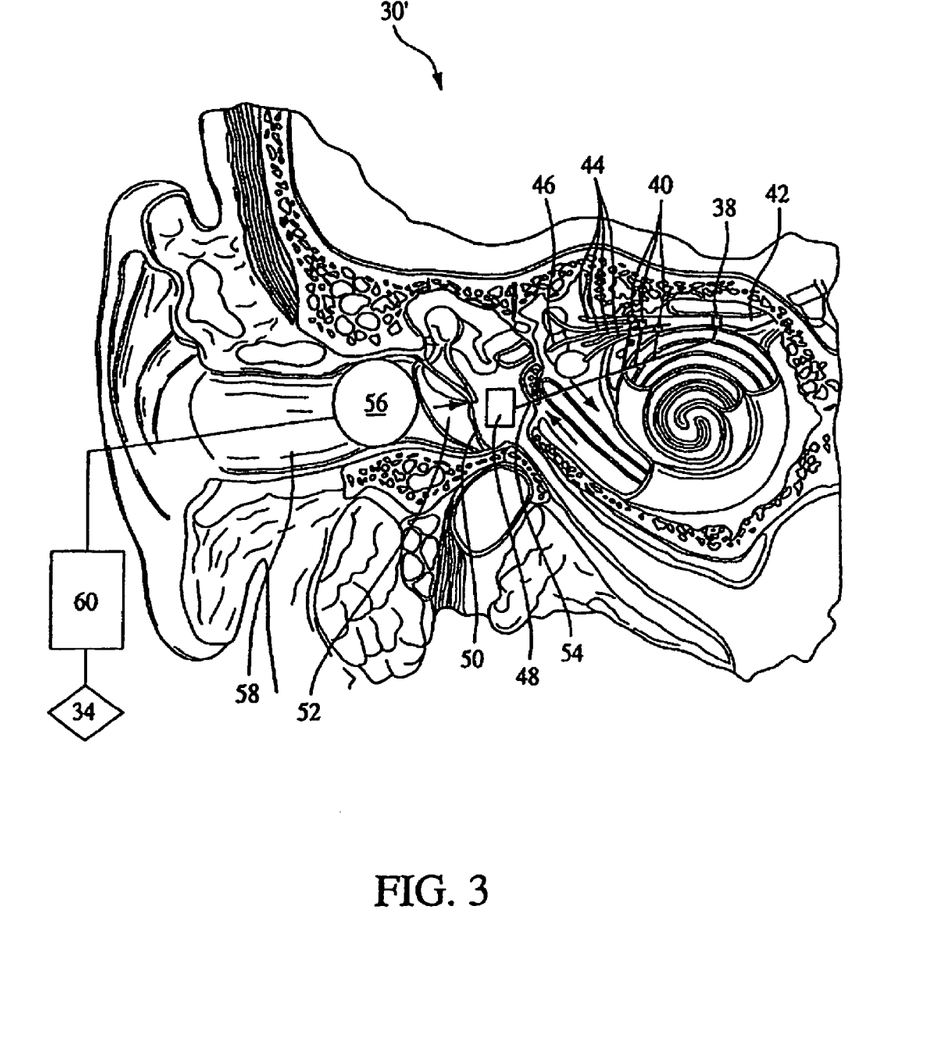
FIG. 3 is a sectional view of a portion of the human anatomy showing the inner ear and schematically showing an invasive vestibular stimulation system according to one embodiment of the invention.
Figure 4:
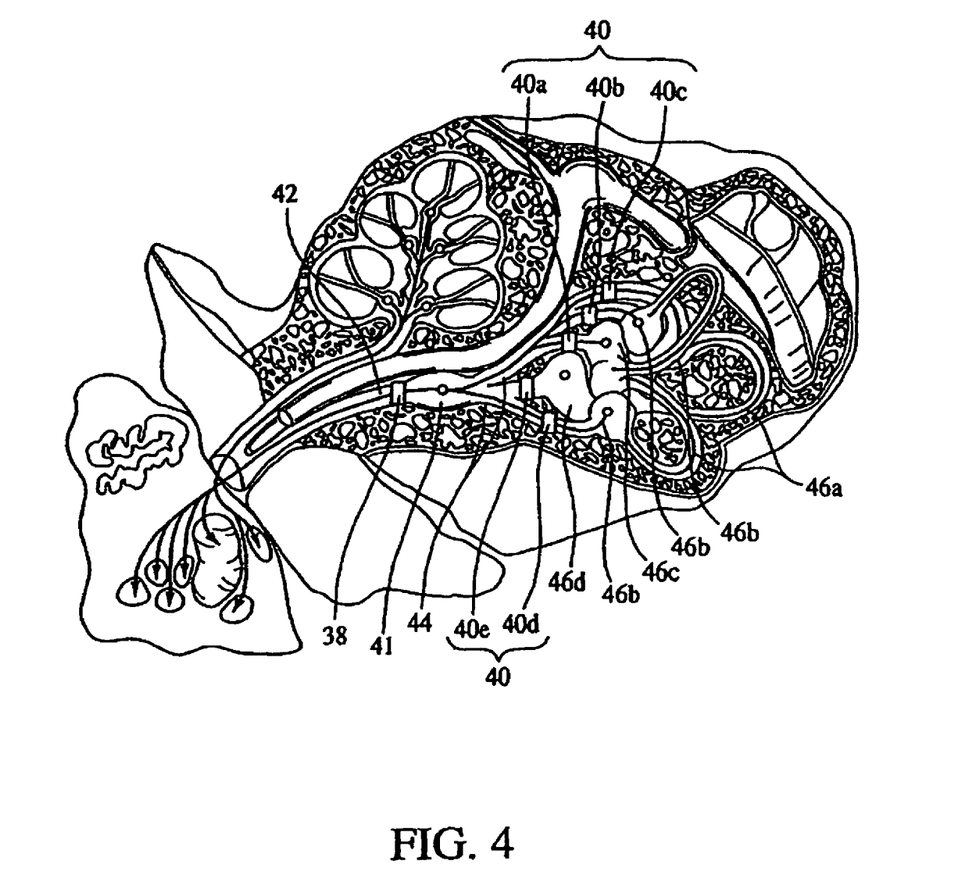
FIG. 4 is a sectional view of a portion of the human anatomy also showing the inner ear and schematically showing the location of stimulation electrodes on the vestibular nerve and nerve branches, in accordance with one embodiment of the invention.

FIGS. 2, 3, and 4 illustrate exemplary embodiments of vestibular stimulation systems 30. In FIG. 2, vestibular stimulation 30 is a completely non-invasive system in that no part of the system is disposed in the patient. Please note that placing a portion of the system, such as the stimulation electrode, in the ear canal is considered to be non-invasive. Vestibular stimulation system 30 in FIG. 2 includes a stimulation element 33 in the form of a surface electrode that, in this exemplary embodiment, is disposed on the surface of the patient just behind the ear so that the electrode generally overlies the vestibular system. The remaining portions of the stimulation system, such as the power supply and the control unit 36, are worn on the ear in the same manner as a conventional hearing aid. When activated, the power supply and control unit 36 energize electrode 33 to send a stimulating current to the patient's vestibular system.

In FIG. 3, vestibular stimulation system 30' is an invasive system that directly stimulates the vestibular nerve and/or its branches. It is considered invasive because at least a portion of the system is disposed internal to the patient. Vestibular stimulation system 30' includes stimulation elements 38 and 40, which are electrodes placed directly on or near vestibular nerve 42 and/or branch nerves 44 that lead to the vestibular nerve. The present invention contemplates that electrodes 38 and/or 40 can be positioned relative to the vestibular nerve 38 and/or a branch nerves 44 associated therewith, respectively, at a variety of locations along these nerves or nerve branches, so long as they are positioned so as to induce stimulation in the associated nerve. For example, electrode 38 can be provided on vestibular ganglion-41. Branch nerves 44 are the nerves coupled to the receptors of the labyrinth associated with the labyrinthine sense, such as the semicircular canals 46*a*, ampullae 46*b*, utricle 46*c*, and saccule 46*d*. Note that the semicircular canals, ampullae, utricle, and saccule are generally identified by numeral 46 in FIG. 3, but are shown in greater detail in FIG. 4. Branch nerves 44 combine to form vestibular nerve 42.

FIG. 4 illustrates in better detail the inner ear and the placement of electrodes 40*a*-40*e* on branch nerves 44 and the placement of electrode 38 on vestibular nerve 42. Electrodes 40*a*-40*e* are generally illustrated in FIG. 3 as electrodes 40. It is to be understood that the number of electrodes and their locations can vary and that electrode stimulators need not be placed on each branch nerve. For example, electrode 38 on vestibular nerve 42 or one or more electrodes 40*a*-40*e* on branch nerves 44 may be eliminated if the desired stimulation effect is achieved by stimulating another nerve or nerves. Ideally, the number of electrodes should be kept to a minimum while providing the desired stimulation effect.

Referring again to FIG. 3, in the illustrated exemplary embodiment, power/control unit 36 of vestibular stimulation systems 30' includes a signal receiving device 48 implanted in tympanic cavity 50 on the interior side of eardrum 52. A signal generator 56 is provided on the exterior side of eardrum 52 in ear canal 58. One or more leads 54 couple signal receiving device 48 to each of electrodes 38 and/or 40 so that each electrode can be energized individually or in any combination. For example, this configuration allows for simultaneous stimulation of multiple electrodes at multiple sites based on a common stimulation source from signal receiving device 48. In addition, this configuration allows for independent control of one or more of the electrodes to provide a great degree of flexibility for the different types of stimulation patterns that can be applied to the patient's vestibular system. For example, the present invention contemplates stimulating between sites, for example, from 40*a* to 40*b*, 40*a* to 40*c*, 40*b* to 40*c*, etc.

Signal generator 56 communicates with signal receiver 48 to cause signal receiver to provide stimulation energy to stimulation electrodes 38 and/or 40. In an exemplary embodiment of the present invention, signal generator 56 generates an electromagnetic field that induces a current in signal receiving device 48, which is then transmitted to electrodes 38 and/or 40. If, however, signal receiving device 48 is provided with its own power supply, the signals from signal generator 56 are command and control signals that dictate how and when the stimulation energy is output from signal receiving device 48. It should be noted that signal generator 56 need not be provided within the ear canal, as shown, if its transmission range is sufficient to transmit greater distances.

The present invention also contemplates doing away with signal receiving device 48 and leads 54 in favor of having an electromagnetic field produced by signal generator 56 directly induce stimulation pulses at the electrodes or at the stimulation site. For example, magnetic stimulation can be used to induce stimulation in the target tissue. In which case, the coil or coils that generate the magnetic field function as signal generator 56, and electrodes 38 and/or 40 can be eliminated. Alternatively, ferromagnetic devices that shape the fields generated by the can be provided at or near the stimulation sites to function in much the same capacity as electrodes 38 and/or 40 to ensure that the target site is adequately and properly stimulated.

The present invention also contemplates that one or more microstimulators, which receive power and data from an external source via rf frequencies, can be implanted in the patient to function as electrodes 38 and/or 40. In which case, the rf oscillator functions as signal generator 56 and is located externally relative to the patient, such as at the patient's bedside.

A power/control unit 60, similar if not identical in function to power/control unit 36 discussed above, causes signal generator 56 to produce the electromagnetic field or other coupling mechanism that initiates stimulation. In the illustrated embodiment, at least one sensor 34 communicates with power/control unit 60 to provide an input signal that is used by the control unit to determine when to generate the electromagnetic field. As discussed in greater detail below, the specific type of sensor or sensors used, and how the control unit uses the received signals to provide stimulation energy to the stimulation elements 38 and/or 40 will depend on the physiological function to be achieved as a result of the stimulation of the vestibular system. Power/control unit 60 is preferably provided outside the patient to simplify recharging or replacing the power supply. Sensor 34 is also typically provided outside the patient. However, sensor 34 may be implanted within the patient if the parameter being monitored requires and/or allows for an invasive location for the sensor.

As noted above, the present invention contemplates stimulating one or more locations in the inner ear associated with the labyrinthine sense, in addition to or in place of direct stimulation of the vestibular nerve and its branches, as shown in FIGS. 2, 3 and 4, in order to provide a therapeutic benefit. That is, it is not necessary that the vestibular nerve or its branches be directly stimulated in order to induce a neural transmission in the vestibular nerve. Because the vestibular nerve is an afferent nerve, and stimulating anything before it involves transduction, stimulation can be provided at one or more sites before the vestibular nerve and still induce the desired neural transmission therein. It should be noted that the term "before" as used in this paragraph refers to portions of the nerve in a direction opposite the direction of normal neural conduction.

Figure 5:
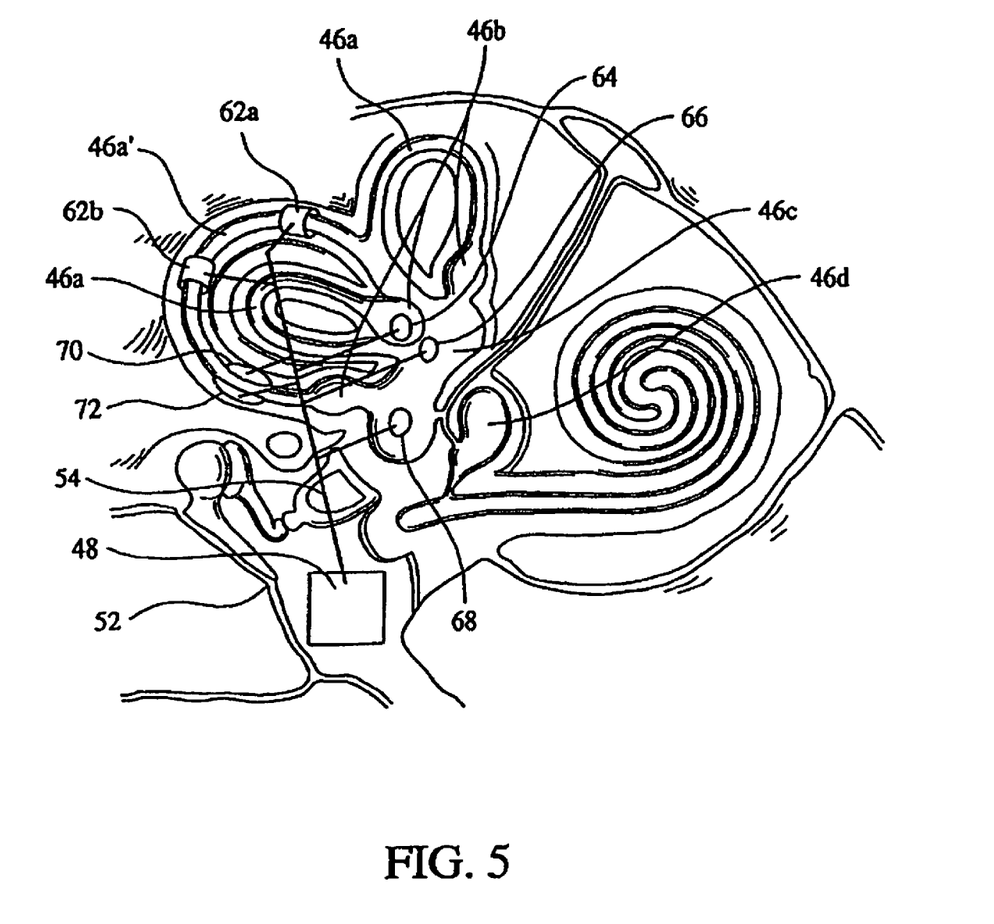
FIG. 5 illustrates a portion of the inner ear showing additional stimulation sites and stimulation elements, in accordance with one embodiment of the invention.

FIG. 5 illustrates a portion of the inner ear showing additional stimulation sites that, once stimulated, induce a neural transmission in the vestibular nerve to provide a therapeutic benefit to the patient. The basic components of the stimulation system shown in FIG. 5 are the same as those illustrated in FIGS. 2-4 except for the stimulation sites. For the sake of illustration, a variety of stimulation devices serving as stimulation element 32 are shown in this embodiment of the present invention. For example, FIG. 5 illustrates a pair of cuffs 62*a* and 62*b* spaced apart from one another and each surrounding a portion of the posterior semicircular canal 46*a'*. Cuffs 62*a* and 62*b* can be electrodes or pressure application devices that exert a force on the semicircular canal. In addition, FIG. 5 illustrates electrodes or pressure application devices 64, 66 and 68 provided on an ampulla 46b, and portions of utricle 46c for stimulating these structures. In addition, FIG. 5 illustrates electrodes or pressure application devices 70 and 72 provided on either side of posterior semicircular canal 46a'. It is to be understood that the present invention contemplates stimulating the outside of the semicircular canals, as shown, as well as stimulating within the semicircular canals. Lead or leads 54 couple signal receiving device 48 to each of these stimulation elements to provide the appropriate stimulation energy or impetus, such as a current in the case of an electrode or an inflating fluid in the case of a pressure application device.

The configuration for vestibular stimulation system 30, 30' shown in FIGS. 2-5 is advantageous in that it minimizes the number and complexity of components that are provided within the patient. It is to be understood that the present invention contemplates that the power supply could include one or more miniature batteries implanted within the patient, rather than the current coupling system shown in the figures. Such an implanted battery system, however, increases the amount of foreign objects that must be disposed within the patient. In addition, if it became necessary to replace the batteries at some point in the future, an additional surgery would be required.

The configuration for vestibular stimulation system 30, 30' shown in FIGS. 2-5 is further advantageous in that no elements of the system are penetrating the patient's tissues from an internal to external location. It is to be understood that the present invention contemplates eliminating signal receiving device 48 and extending leads 54 outside the body, such as through the eardrum or through the surrounding tissue, for providing energy to the electrodes. Alternatively, the present invention contemplates that electrodes 38 and/or 40 are relatively stiff needle electrodes that insert through the eardrum, for example, with the distal end remaining outside the patient. In these configurations, leads or electrodes must physically pass from an interior location within the patient to an exterior location so that they can be coupled to the power/control unit. While this embodiment provides a good path of conduction for the stimulation energy and minimizes the amount of foreign objects located within the patient, when a foreign object extends through the patient's tissue, providing a path from the interior to the exterior of the patient, this represents a potential site for infection or provides a pathway by which infections may enter the body.

While FIGS. 2, 3, and 4 illustrate an electrode stimulation system, it is to be understood that any of the above-described stimulation techniques can be employed to stimulate the patient's vestibular system. For example, electrodes 38 and/or 40 can be replaced with pressure cuffs to apply a physical pressure on the vestibular sensory tissue. As will be understood from the following discussions of the hypothalamic responses that can be achieved by the stimulation system of the present invention, the present invention contemplates stimulating sites within the inner ear other than or in addition to the nerve stimulation sites shown in FIGS. 2, 3, and 4. For example, the same stimulation effect accomplished by stimulating the vestibular nerve directly may be accomplished by globally stimulating the portions of the labyrinth associated with the labyrinthine sense. Please refer to FIG. 5 for a discussion of other exemplary stimulation sites of the present invention.

In one variation of this embodiment, signal receiving device 48 communicates with signal generating device 56, as indicated by arrow A, to transmit information regarding one or more physiological functions from signal receiving device 48 to signal generating device 56, which is based on the output from response module, so that power/control unit 60 provides the appropriately timed stimulation energy to the vestibular system. Another variation of this embodiment contemplates that the signal receiving device itself controls the application of stimulation energy to the vestibular system based on the output from response module 34. In which case, a constant supply of stimulation energy is preferably delivered by signal generating device 56 to signal receiving device 48 so that stimulation energy is always available when signal receiving device 48 determines that stimulation is to be applied.

In addition, the present invention contemplates providing appropriate alarms and other monitoring functions to monitor the patient an/or the condition of the stimulation system and communicate the monitored information to a caregiver and/or to a storage device, so that emergency conditions, such as failure of the vestibular stimulation system can be detected and reported. In addition, information on the use and function of the stimulation system can be obtained and recorded.

In one embodiment of the invention, by stimulating the vestibular organs (e.g., with vestibular stimulation system 30, 30') other areas of the brain linked to the vestibular system can be influenced. More specifically, the hypothalamus, among other areas, can be influenced. Connections between the vestibular system and the hypothalamus include direct connections and indirect connections via other regions of the brain. One example of a direct connection between the hypothalamus and the vestibular system includes the transmission of information processed in the superior vestibular nucleus and the lateral vestibular nucleus directly to the hypothalamus, where the transmitted information is used to control vestibulo-autonomic reflexes. Another example of a direct connection includes the enervation of the posterior hypothalamus by vestibular nuclei, which also plays a role in vestibular mediation of autonomic function.

While such direct monosynaptic connections between the vestibular system and the hypothalamus may be relatively few in number, and may not exert much influence over the hypothalamus, there are significant indirect connections between the two regions. These indirect connections include instances in which the vestibular nuclei project to other brainstem regions, which then project to the hypothalamus. Some of these nuclei connected directly with the vestibular system influence autonomic functions, via the hypothalamus, such as circadian and homeostatic functions. These nuclei include the parabrachial nucleus, the caudal raphe nuclei, the solitary nucleus, and the locus coeruleus. Other nuclei under vestibular influence, such as the amygdala and the infralimbic cortex, may be stimulated by the vestibular system to send information that gets processed by limbic structures before influencing the hypothalamus directly.

The areas of the hypothalamus that can be affected indirectly by the vestibular system influence a variety of physiological functions via an array of mechanisms. One such mechanism is the release of orexin neurons (also known as hypocretin). Orexin neurons have been tied to sleep, metabolism, thermoregulation, vasoplastic function, and hormonal release, among other physiological functions. The release of orexin neurons also alleviates effects of anxiety. The effects of anxiety include physiological effects such as cardiovascular effects (e.g., increased pulse, increased blood pressure, etc.), changes in body temperature, metabolic effects (e.g., loss of appetite, loss of energy, etc.), and sleep pattern effects (e.g., insomnia, hypersonmia, etc.), as well as psychological effects (e.g., sense of dread, paranoia, inability to concentrate, etc.).

As was mentioned briefly above, the hypothalamus includes several neurons responsible for secreting various hormones. The hormones whose secretion is controlled by the hypothalamus include thyrotropin-releasing hormone, gonadotropin-releasing hormone, growth hormone-releasing hormone, corticotropin-releasing hormone, somatostatin, dopamine, antidiuretic hormone, and oxytocin.

Referring back to FIG. 1, in one embodiment of the invention, vestibular stimulation system 30 may be implemented to stimulate the vestibular system of a patient so as to elicit a desired response from the hypothalamus. The desired response of the hypothalamus may include regulating one or more physiological functions under the influence of the hypothalamus, including the regulation of a secretion of one or more hormones whose secretion is controlled by the hypothalamus, and/or regulating one or more psychological functions, such as alleviating an anxiety level of an individual. However, because of the indirect nature of the pathways by which the vestibular system influences the hypothalamus, and the cortical interaction that takes place along these pathways, a response of the hypothalamus to a given application of stimulation to the vestibular system may be a function of the individual brain functions of the patient, and may be unique to each patient. Therefore, in order to elicit the desired response from the hypothalamus, response module 34 may monitor one or more physiological functions regulated by the hypothalamus in response to the stimulation applied to the vestibular system of the patient so that the response of the hypothalamus may be implemented in a feedback manner to "tune" the stimulation applied by vestibular stimulation system 30. This enables the desired response of the hypothalamus can be attained and maintained.

In one embodiment of the invention, response module 34 is capable of receiving a subjective input from the patient (or another individual) based upon a perceived response of the hypothalamus. For example, in one embodiment, response module 34 includes an input device capable of receiving information from the patient. The input device may include, for instance, a keyboard, a mouse, a joystick, a keypad, a switch, a dial, a knob, or any other device that would enable an individual to input information to response module 34. In one embodiment, stimulation designed to elicit a desired response from the hypothalamus of the patient is applied to the vestibular system of the patient via stimulation element 32. The desired response include the regulation of a set of one or more physiological functions in a predetermined manner. Due to the stimulation, the vestibular system influences the hypothalamus, eliciting an actual response of the hypothalamus that is manifested in the regulation of various physiological functions of the patient. If the actual response of the hypothalamus is different than the desired response, then the patient inputs that the response achieved is not the desired response, and power/control unit 36 adjusts the stimulation being applied by stimulation element 32 accordingly.

In one embodiment of the invention, the input device enables the patient to input to response module 34 whether the patient perception of the actual response of the hypothalamus includes regulating the set of physiological functions included in the desired response. For example, if the desired response of the hypothalamus includes reducing an anxiety level, but the actual response of the hypothalamus to the vestibular stimulation, as perceived by the patient, does not include influencing the anxiety level, the patient inputs this disparity between the perceived response of the hypothalamus and the actual response of the hypothalamus. Based on this input, power/control unit 36 adjusts the stimulation being applied to the vestibular system to attempt to elicit the desired response from the hypothalamus.

In one embodiment of the invention, when the actual response includes regulating the subset of physiological functions included in the desired response, the input device enables the patient to input to response module 34 whether the magnitude of the change(s) in the physiological functions in the actual response, as perceived by the patient, match a desired magnitude of the changes in the physiological functions in the desired response. For instance, when the desired response of the hypothalamus includes reducing the anxiety level of the patient by a desired amount, but the perceived response of the hypothalamus includes reducing the anxiety level of the patient by less than the desired amount, the patient can input this deficiency in the perceived response of the hypothalamus via the input device.

In one embodiment of the invention, response module 34 includes one or more sensors for detecting one or more physiological correlates to the physiological effects and/or psychological effects in the desired response of the hypothalamus. The detections of the sensors are then used to determine an actual response of the hypothalamus. The actual response is then used by power/control unit 36 to adjust the stimulation being applied to the patient's vestibular system via stimulation element 32. In one embodiment, the sensors include a sensor (or sensors) capable of monitoring autonomic functions. For instance, the sensors may measure various expressions of autonomic functions. Some examples of measurements that may be taken by the sensors to monitor the autonomic functions of the patient include a vascular tone measurement, a core temperature measurement, a metabolic function measurement, a pulse rate measurement, a galvanic skin response measurement, a heart rate variability measurement, a baroreceptor sensitivity measurement, a body weight measurement, a muscle sympathetic nerve activation measurement, a pupillary dilation measurement, a measurement of peristaltic movement of materials through the digestive system, and/or a blood pressure measurement.

In one embodiment of the invention, one or more aspects of the stimulation applied by stimulation element 32 to the patient's vestibular system is measured. For example, an amount of energy included in the stimulation energy and/or a rate at which the stimulation energy is applied that is applied to the vestibular system from stimulation element 32. For instance, in one embodiment, stimulation element 32 applies an electrical energy to the vestibular stimulation, and the stimulation energy is measured in terms of a potential (e.g., in volts). In another embodiment, the stimulation is measured in terms of a reaction by the patient to the stimulation energy. For example, the stimulation may be measured in terms of an amount of sway experienced by the patient as a result of the stimulation. The sway may be measured using a conventional balance plate mechanism.

In one embodiment of the invention, the measurement of the stimulation enables the amount and/or rate at which the stimulation energy is being applied to the patient to be represented to an individual (e.g., the patient, a caregiver, etc.). Adjustments to the stimulation can be affected by the individual based on this representation. In one embodiment, the adjustments to the stimulation are affected by the individual by inputting the desired adjustments into the input device associated with response module 34.

In one embodiment of the invention, the aspects of the stimulation is measured by power/control unit 36. Power/control unit 36 measures the aspects of the stimulation, and then uses the measured values to determine adjustments that should be made to the stimulation based on the response of the hypothalamus to the stimulation, as determined by response module 34.

Figure 6:
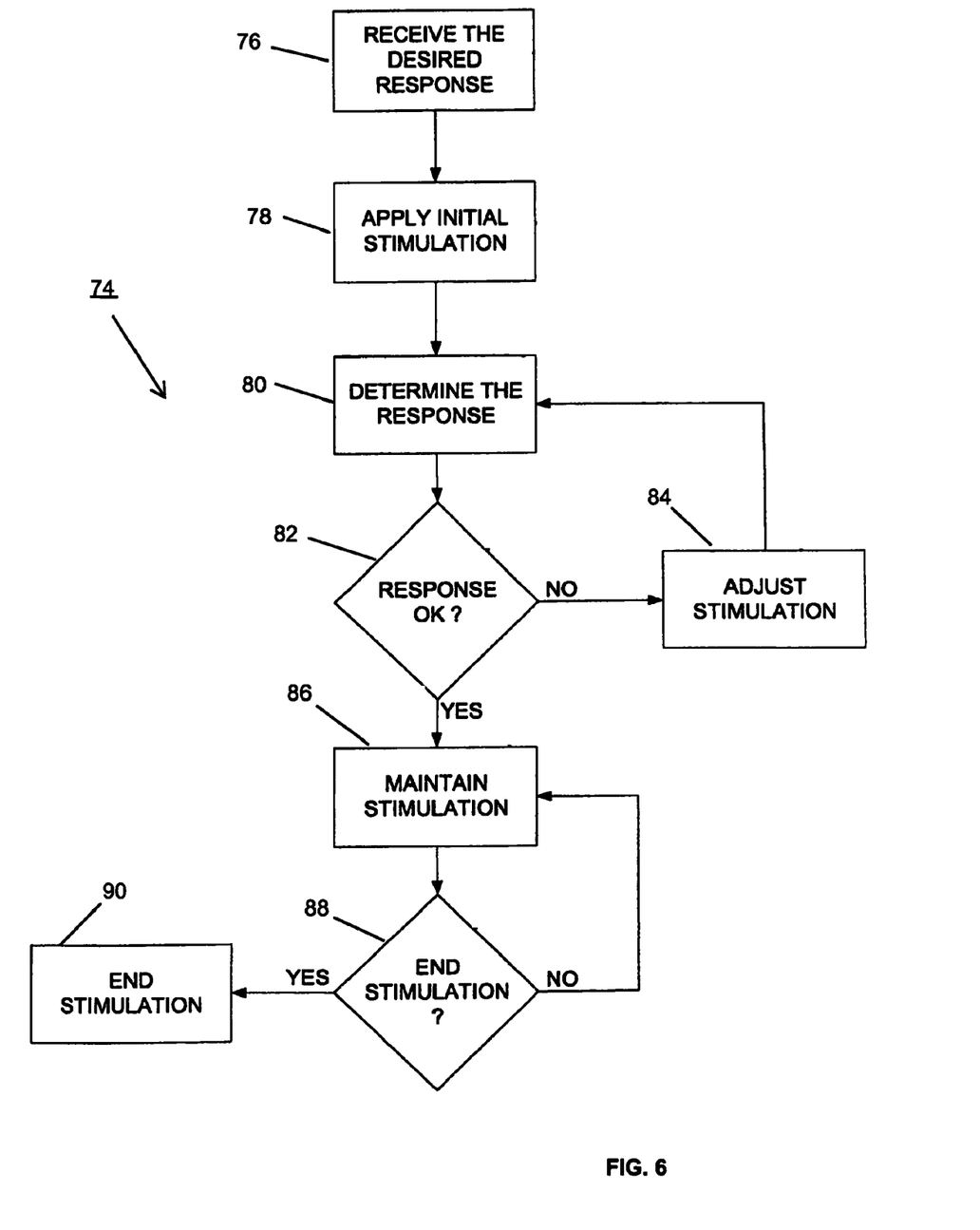
FIG. 6 is a flowchart illustrating a method of regulating a response of a hypothalamus of a patient, according to one embodiment of the invention.

FIG. 6 is an exemplary illustration of a method 74 of regulating a response of a hypothalamus of a patient according to one embodiment of the invention. In one embodiment of the invention, method 74 may be executed by system 30. However, it should be appreciated that in other embodiments of the invention, method 74 may be executed by other systems, such as system 30' or another system, without departing from the scope of the invention.

At a step 76, a desired response of the hypothalamus is received. In one embodiment, the desired response of the hypothalamus is received at an input device associated with the system. For example, an input device associated with one or both of response module 34 and power/control unit 36, as described above, may be used by an individual (e.g., the patient, a caregiver, etc.) to input the desired response to system 30. The desired response may include any of the responses of the hypothalamus set forth above, including, for example, the regulation of a set of one or more physiological functions of the patient. The physiological functions may include, for instance, cardiovascular functions (e.g., increased pulse, increased blood pressure, etc.), thermal functions, metabolic functions (e.g., appetite, energy level, etc.), sleep functions (e.g., fatigue, insomnia, hypersomnia, etc.), and/or psychological functions (e.g., an anxiety level, etc.).

An initial stimulation is applied by the system to the vestibular system of the patient at a step 78. In one embodiment, the initial stimulation is applied to the vestibular system by stimulation element 32, as was described previously. One or more aspects of the initial stimulation, such as a timing, level, pattern, pulse width, pulse duration, pulse shape, or frequency of the stimulation are controlled by power/control unit 36 such that the stimulation applied to the vestibular system via stimulation element 32 is designed to elicit the desired response from the hypothalamus.

At a step 80, a response of the hypothalamus to the stimulation of the vestibular system is determined. In one embodiment of the invention, step 80 includes receiving a subjective input based on a perceived response of the hypothalamus made by the patient, as was described above. In one embodiment, step 80 includes detecting of one or more physiological correlates to the set of physiological functions included in the desired response of the hypothalamus. The detections are made by one or more sensors included in response module 34, as was set forth previously. In one embodiment, step 80 includes both receiving a subjective input based on a perceived response of the hypothalamus and detecting physiological correlates to the set of phsyiological functions with sensors included in response module 34.

The determined response and the desired response are compared at a step 82. More particularly, a determination is made as to whether the response of the hypothalamus to the stimulation of the vestibular system, as determined at step 80, corresponds in a satisfactory manner with the desired response. In one embodiment of the invention, this comparison is made by power/control unit 36. If the comparison between the response determined at step 80 and the desired response do not correspond to each other, then method 74 proceeds to a step 84. The response of the hypothalamus determined at step 80 (or the "actual response" of the hypothalamus) and the desired response of the hypothalamus do not correspond to each other if either the actual response of the hypothalamus does not effect the set of physiological functions included in the desired response or because the set of physiological functions effected are not effected by the appropriate amount (e.g., a vascular tone is decreased by less than a desired amount). In instances where the actual response does not correspond to the desired response, one or more differences between the actual response and the desired response may be determined. For example, in one embodiment, a difference between the actual response and the desired response may include one or more physiological functions included in the desired response that are not included in the actual response. In one embodiment, a difference between the actual response and the desired response may include a magnitude difference between a desired effect on a particular physiological function included in the desired response and the actual effect on the particular physiological fiction.

At step 84 the stimulation applied by stimulation element 32 to the vestibular system is adjusted. In one embodiment of the invention, the stimulation is adjusted by power/control unit 36. Adjusting the stimulation includes adjusting one or more aspects of the stimulation in order to attempt to adjust the actual response of the hypothalamus so that the actual response will correspond to the desired response. In one embodiment, the adjustment of the one or more aspects of the stimulation is based on the differences between desired response of the hypothalamus and the actual response of the hypothalamus to the stimulation. From step 84, method 74 returns to step 80.

If, at step 82, it is determined that the actual response of the hypothalamus to the stimulation corresponds to the desired response of the hypothalamus, then method 74 proceeds to a step 86. At step 86, the stimulation is maintained and method 74 proceeds to a step 88. At step 88 a determination is made as to whether the stimulation should be continued. This determination is controlled by input from an individual, such as the patient. For example, if the individual inputs a deactivation (or "power off") command, then method 74 proceeds to a step 90 where stimulation of the vestibular system is ended. In one embodiment, the determination made at step 88 is made by power/control unit 36. Method 74 proceeds to step 90 if it is determined at step 88 that the patient has received stimulation for a predetermined period of time. At step 90, the stimulation is ended. However, if the stimulation is to be continued, method 74 returns to step 86.

Figure 7:
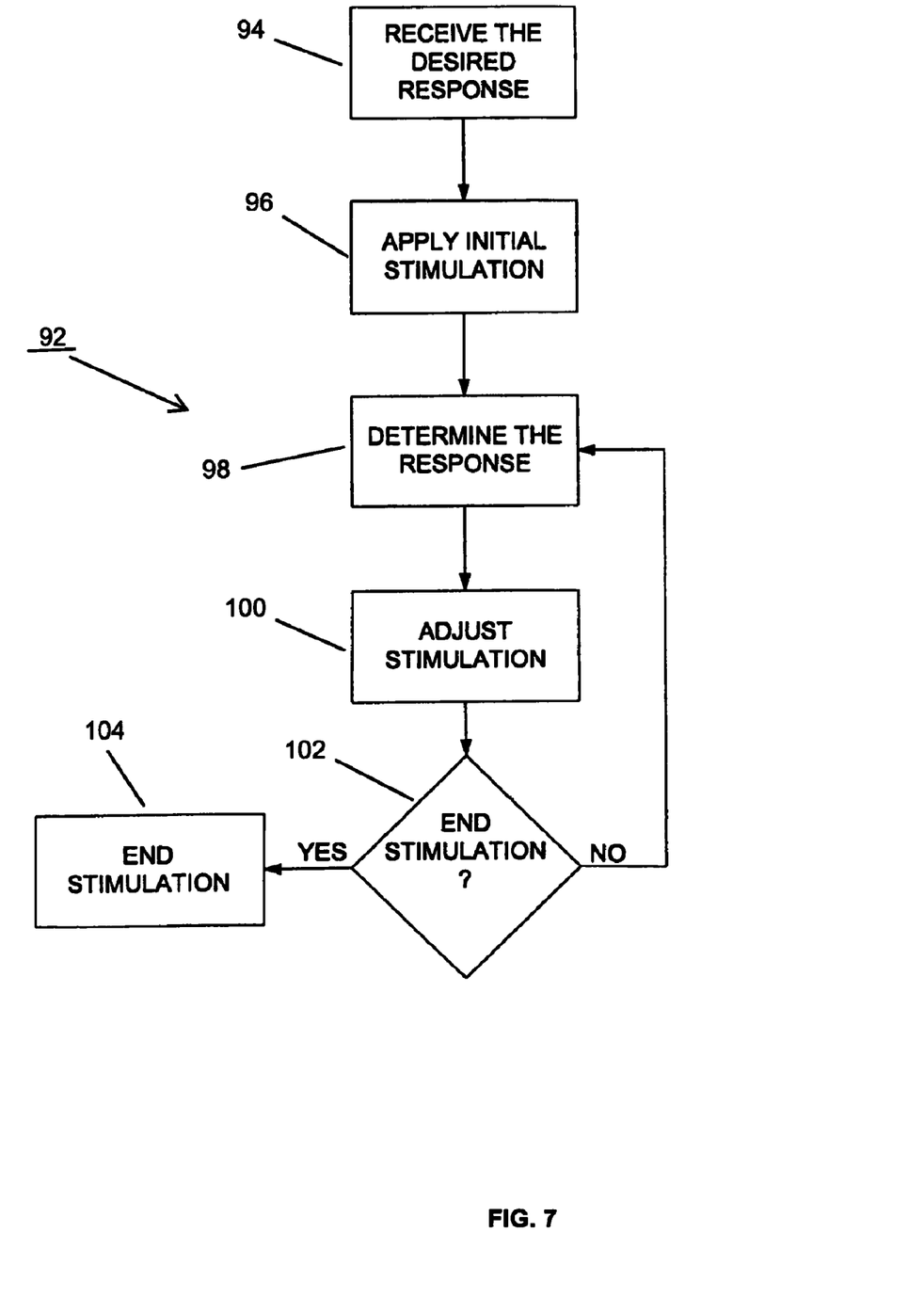
FIG. 7 is a flowchart illustrating another method of regulating a response of a hypothalamus of a patient, according to one embodiment of the invention.

FIG. 7 illustrates a method 92 of regulating a response of a hypothalamus of a patient, in accordance with one embodiment of the invention. In one embodiment, steps 94, 96, and 98 in method 92 correspond to steps 76, 78, and 80, respectively, in method 74, and provide the same functionality as was described previously. In one embodiment, steps 94, 96, and 98 are executed by the same components of system 30 as steps 76, 78, and 80, as set forth previously. From step 98, method 92 proceeds to a step 100, at which stimulation being applied to the patient's vestibular system is adjusted. The adjustment made at step 100 is made based on differences between the actual response of the hypothalamus of the patient, determined at step 98, and the desired response of the hypothalamus, received at step 94. In one embodiment, the adjustment is made in the manner described above with respect to step 84 of method 74, and is made by power/control unit 36. In instances in which the actual response of the hypothalamus and the desired response correspond, the adjustment to the stimulation made at step 100 will be effectively zero.

From step 100, method 92 proceeds to a step 102, at which a determination is made as to whether stimulation should be continued. In one embodiment, the determination made at step 102 corresponds to the determination made at step 88 of method 74, described above, and is based on similar variables. In one embodiment, the determination of step 102 is made by power/control unit 36. If the stimulation is to be continued, method 92 proceeds to step 98 and step 100 to again determine an actual response of the hypothalamus to the stimulation, and adjust the stimulation based on the determined actual response. As may be appreciated, this is different than method 74. Referring back to FIG. 6, in method 74, if it is determined at step 88 that the stimulation should be continued, stimulation is simply maintained at step 86 without re-determining the actual-response of the hypothalamus to the stimulation, and then adjusting the stimulation based on this newly determined actual response. Returning to FIG. 7, if it is determined at step 102 that the stimulation should be ended, method 92 proceeds to step 104 where the stimulation is ended. In one embodiment of the invention, the stimulation is ended by power/control unit 36, which controls stimulation element 32 to stop the stimulation.

In other embodiments of the invention, other variations on methods 74 and 92 are implemented to elicit a desired response from the patient's hypothalamus by stimulating the patient's vestibular system. It should be appreciated that such variations are contemplated, and fall within the scope of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for influencing a hypothalamus of an individual to alleviate an anxiety level of the individual, the method comprising:

applying an electrical stimulation to at least a portion of the vestibular system of an individual via one or more removable superficial electrodes, wherein the stimulation is applied to elicit a desired response from the hypothalamus that reduces the anxiety level of the individual;

receiving a subjective input indicating a perceived response of the hypothalamus to the stimulation in affecting the anxiety level of the individual; and controlling the stimulation based on the received subjective input.

2. The method of claim 1, wherein the applied stimulation comprises a therapeutic non-invasive electrical energy stimulation to a skin surface of the individual adjacent to at least a portion of the vestibular system of the individual.

3. The method of claim 1, wherein the anxiety level comprises: an emotional anxiety level, a psychological anxiety level, or any combination thereof.

4. The method of claim 1, further comprising:

obtaining the desired response of the hypothalamus in reducing the anxiety level of the individual;

comparing the desired response to the subjective input indicating the perceived response;

wherein controlling the stimulation based on the received subjective input is based on the comparison.

* * * * *